United States Patent
Sakai et al.

(10) Patent No.: US 10,354,372 B2
(45) Date of Patent: Jul. 16, 2019

(54) DEFECT INSPECTION METHOD AND APPARATUS

(71) Applicant: HITACHI POWER SOLUTIONS CO., LTD., Hitachi-shi, Ibaraki (JP)

(72) Inventors: Kaoru Sakai, Tokyo (JP); Osamu Kikuchi, Hitachi (JP); Kenji Sahara, Hitachi (JP)

(73) Assignee: HITACHI POWER SOLUTIONS CO., LTD., Ibaraki (JP)

( * ) Notice: Subject to any disclaimer, the term of this patent is extended or adjusted under 35 U.S.C. 154(b) by 0 days.

(21) Appl. No.: 15/287,418

(22) Filed: Oct. 6, 2016

(65) Prior Publication Data

US 2018/0101944 A1    Apr. 12, 2018
US 2019/0050978 A9    Feb. 14, 2019

(30) Foreign Application Priority Data

Oct. 8, 2015   (JP) .................................. 2015-200089

(51) Int. Cl.
*G06T 7/00*  (2017.01)
*G01N 29/06*  (2006.01)
(Continued)

(52) U.S. Cl.
CPC ....... *G06T 7/0004* (2013.01); *G01N 29/0654* (2013.01); *G01N 29/265* (2013.01);
(Continued)

(58) Field of Classification Search
CPC . G06T 2207/30148; G06T 2207/10132; G06T 7/001; G06T 2207/10012;
(Continued)

(56) References Cited

U.S. PATENT DOCUMENTS 4,510,810 A    4/1985  Kanda et al.
5,574,800 A *  11/1996  Inoue ............... G01N 21/95607
                                                     382/149
(Continued)

FOREIGN PATENT DOCUMENTS

JP    S58-122456 A    7/1983
JP    2007-101320 A   4/2007
(Continued)

OTHER PUBLICATIONS

English language translation of Japanese Office Action dated Feb. 13, 2019 for JP Patent Application No. 2015-200089.
(Continued)

*Primary Examiner* — Bobbak Safaipour
(74) *Attorney, Agent, or Firm* — Miles & Stockbridge PC

(57) ABSTRACT

In an ultrasonic inspection performed on an inspection object including a fine and multi-layer structure such as a semiconductor wafer and a MEMS wafer, a defect is detected by: separating a defect present inside from a normal pattern; obtaining an image of the inspection object by imaging the inspection object having a pattern formed thereon to enable a highly sensitive detection; generating a reference image that does not include a defect from the obtained image of the inspection object; generating a multi-value mask for masking a non-defective pixel from the obtained image of the inspection object; calculating a defect accuracy by matching the brightness of the image of the inspection object and the reference image; and comparing the calculated defect accuracy with the generated multi-value mask.

14 Claims, 13 Drawing Sheets

(51) Int. Cl.
　　　*G01N 29/265*　　　(2006.01)
　　　*H01L 21/66*　　　(2006.01)
(52) U.S. Cl.
　　　CPC .............. *G06T 7/001* (2013.01); *H01L 22/12* (2013.01); *H01L 22/20* (2013.01); *G01N 2291/044* (2013.01); *G06T 2207/10132* (2013.01); *G06T 2207/30148* (2013.01)
(58) Field of Classification Search
　　　CPC . G06T 2207/10028; G06T 2207/10061; G06T 7/0006; G06T 7/0004
　　　See application file for complete search history.

(56) References Cited

U.S. PATENT DOCUMENTS

| | | | | |
|---|---|---|---|---|
| 5,774,574 | A * | 6/1998 | Hoki | G06T 7/001 348/129 |
| 6,285,783 | B1 * | 9/2001 | Isomura | G06T 7/0002 382/140 |
| 6,842,245 | B2 * | 1/2005 | Ando | H01L 22/34 356/237.1 |
| 2003/0179921 | A1 * | 9/2003 | Sakai | G06T 7/0002 382/151 |
| 2004/0124363 | A1 * | 7/2004 | Yoshida | G01N 21/95684 250/372 |
| 2005/0100206 | A1 | 5/2005 | Imi | |
| 2005/0142455 | A1 * | 6/2005 | Ando | G03F 1/84 430/5 |
| 2007/0177787 | A1 * | 8/2007 | Maeda | G06K 9/00557 382/141 |
| 2010/0098322 | A1 * | 4/2010 | Inoue | G06T 7/001 382/144 |
| 2011/0211754 | A1 | 9/2011 | Litvak et al. | |
| 2011/0274342 | A1 * | 11/2011 | Maeda | G01N 21/95623 382/149 |
| 2012/0304773 | A1 | 12/2012 | Horibe et al. | |
| 2013/0082174 | A1 * | 4/2013 | Chen | H01L 22/12 250/307 |
| 2014/0133774 | A1 * | 5/2014 | Chen | H04N 5/3675 382/263 |
| 2014/0148689 | A1 | 5/2014 | Lee et al. | |
| 2014/0165236 | A1 * | 6/2014 | Budach | G03F 1/22 850/9 |
| 2015/0125067 | A1 | 5/2015 | Isomura et al. | |
| 2015/0355105 | A1 | 12/2015 | Yamashita | |
| 2017/0004360 | A1 * | 1/2017 | Tanaka | G06K 9/036 |

FOREIGN PATENT DOCUMENTS

| | | |
|---|---|---|
| JP | 2012-253193 A | 12/2012 |
| JP | 2013-213681 A | 10/2013 |
| TW | 200527321 A | 8/2005 |
| WO | 2014-112290 A | 1/2017 |

OTHER PUBLICATIONS

Non-Final Office Action dated Apr. 2, 2019 for U.S. Appl. No. 16/289,404.

* cited by examiner

F I G. 1
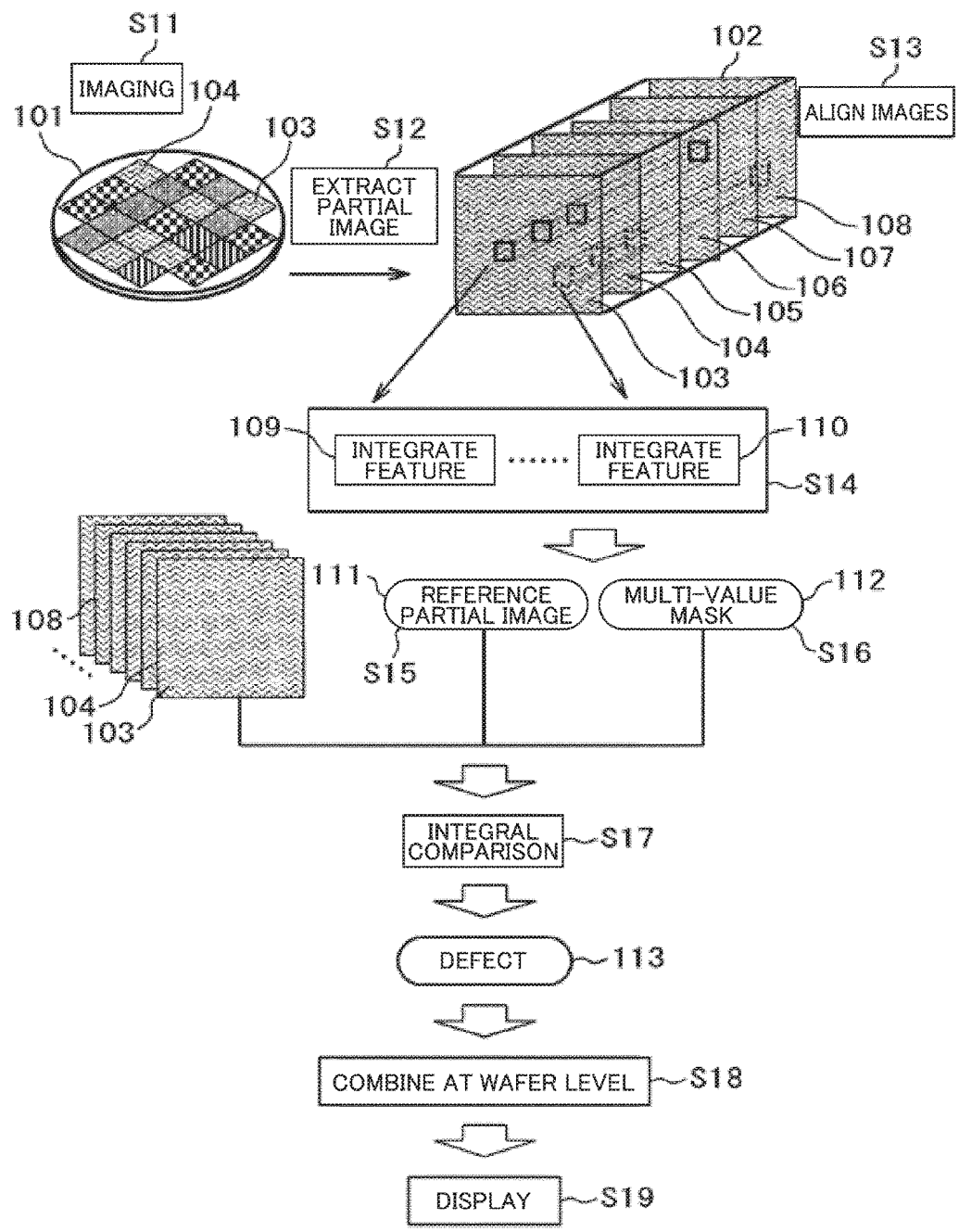

F I G. 5 A
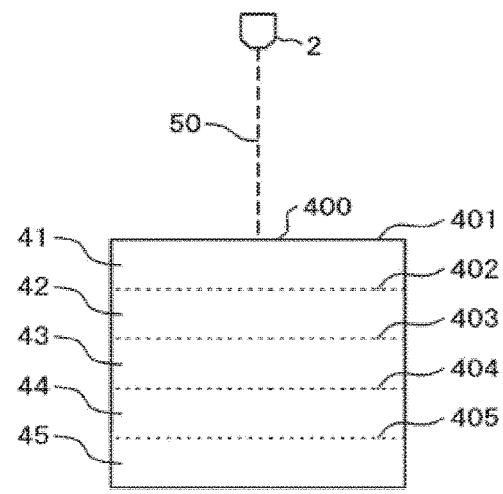
F I G. 5 B
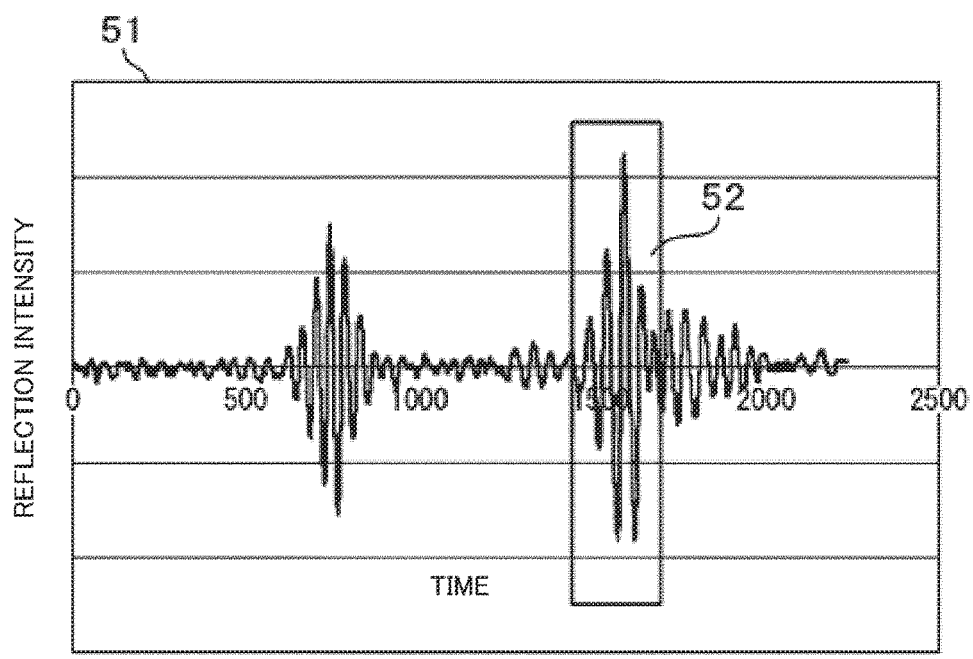

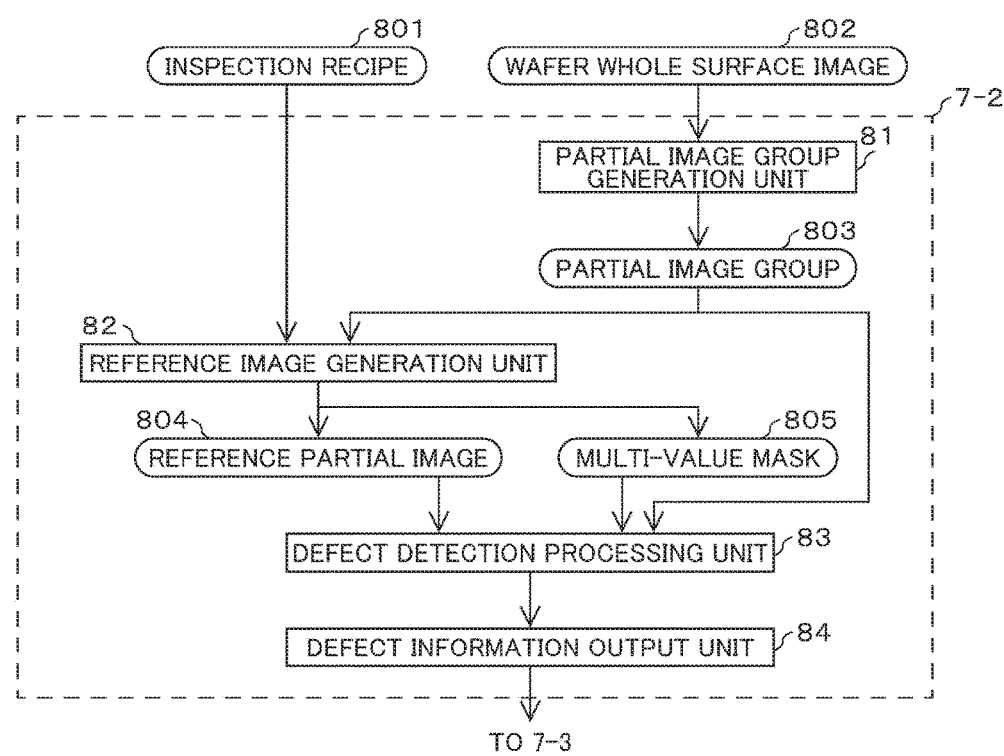
F I G. 8

DEFECT INSPECTION METHOD AND APPARATUS

BACKGROUND

The present invention relates to an apparatus for inspecting a defect from an image of an inspection object obtained by using an ultrasonic wave, an x-ray, or the like, and specifically to an inspection method suitable for an inspection of an inspection body having a multi-layer structure and a non-destructive inspection apparatus using the same.

As a non-destructive inspection method for inspecting a defect from an image of an inspection object, there are a method of using an ultrasonic image generated by irradiating the inspection object with an ultrasonic wave and detecting a reflected wave therefrom, and a method of using an x-ray image obtained by irradiating the inspection object with an x-ray and detecting an x-ray transmitted therethrough.

In order to detect a defect present in an inspection object having a multi-layer structure using an ultrasonic wave, a reflection property due to difference in acoustic impedance is generally used. The ultrasonic wave propagates through a liquid or solid material and generates a reflected wave at an interface between materials having different acoustic impedances or at a cavity. Since a reflected wave from a defect is different from a reflected wave from a defect-free portion in its strength, it is possible to obtain an image that exposes the defect present in the inspection object by visualizing reflection intensities at inter-layer interfaces of the inspection object.

Determination of presence of a defect in the obtained image of the reflection intensity is often performed visually by an inspector, which may lead to variation in the evaluation result due to the experience of each inspector. Moreover, major inspection objects such as semiconductors and electronic devices are increasingly miniaturized, making it more difficult to visually distinguish a defect from a normal pattern. Furthermore, multi-layer structures have become more popular to be adapted to multi-functionalization and miniaturization of mounting products, a WLP (Wafer Level package) method of handling the product in a form of a wafer until the final process of packaging is becoming a mainstream in the manufacturing scene. Thus, it is required for the ultrasonic inspection to detect a micron-order internal defect at a high speed with high sensitivity by separating the micron-order internal defect from a complicated pattern in the form of the wafer. However, this corresponds to detecting only a few pixels showing the defect from several tens of millions of pixels constituting an internal image, which is nearly impossible to be determined visually.

One conventional technique of automatically detecting a defect from an ultrasonic inspection image is a method described in Japanese Patent Laid-open No. 2007-101320 (Patent Document 1). This includes a function of sequentially generating and displaying ultrasonic inspection images, thereby extracting a candidate defect based on contiguity of a luminance distribution in each image. A defect and a noise can be distinguished by the length of the continuous repetition of the candidate defect. Furthermore, there is another method described in Japanese Patent Laid-open No. 2012-253193 (Patent Document 2). In this method, a presence of a void in a TSV (Through Silicon Via) in a three-dimensional integration structure is estimated based on ultrasonic scanning.

SUMMARY

In a case where the inspection object has a complicated pattern, as well as a multi-layer structure, of a semiconductor or an electronic device, then it is possible to distinguish a defect having a certain length and a noise generated at random times using the method described in Japanese Patent Laid-open No. 2007-101320, but impossible to distinguish between a fine defect from a normal pattern. With the method described in Japanese Patent Laid-open No. 2012-253193, the pattern of the inspection object is limited to the TSV, and in order to avoid an effect by a structure that may reduce resolution of the TSV in the vertical direction (bump electrode or wiring layer), the presence of the void in an active TSV is presumed by forming a TEG (Test Element Group) region including only an etch stop layer and the TSV and inspecting the presence of the void in the TEG region, which cannot inspect a wafer whole surface including a mixture of various patterns.

It is therefore an object of the present invention to provide an inspection method and an inspection apparatus capable of detecting an internal fault with a high sensitivity by separating it from a normal pattern in an ultrasonic inspection performed on an inspection object including a fine and multi-layer structure such as a semiconductor wafer and a MEMS wafer.

To address the above problem, the present invention provides a defect inspection method of detecting a defect including the steps of: obtaining an image of an inspection object by imaging the inspection object having a pattern formed thereon; generating a reference image that does not include a defect from the obtained image of the inspection object; generating a multi-value mask for masking a non-defective pixel from the obtained image of the inspection object; calculating a defect accuracy by matching the brightness of the image of the inspection object and the reference image; and comparing the calculated defect accuracy with the generated multi-value mask.

To address the above problem, the present invention also provides a defect inspection apparatus including: an image acquisition unit obtaining an image of an inspection object by imaging the inspection object having a pattern thereon; a reference image generation unit generating a reference image that does not include a defect from the image of the inspection object obtained by the image acquisition unit and generating a multi-value mask for masking a non-defective pixel from the obtained images of the inspection object; a feature amount computing unit calculating a defect accuracy by matching the brightness of the image of the inspection object obtained by the image acquisition unit and the reference image generated by the reference image generation unit; and a defect detection processing unit detecting the defect by comparing the defect accuracy calculated by the feature amount computing unit with the multi-value mask generated by the reference image generation unit.

Moreover, to address the above problem, the present invention further provides an ultrasonic inspection apparatus including: a detection unit including an ultrasonic probe emitting an ultrasonic wave and a flaw detector detecting a reflected echo generated from an inspection object by the ultrasonic wave emitted from the ultrasonic probe; an A/D conversion unit A/D converting a signal output from the flaw detector having detected the reflected echo in the detection unit; and an image processing unit detecting the reflected echo from the flaw detector converted into a digital signal by the A/D conversion unit, processing the output signal, generating a sectional image in a plane parallel with a surface of the inspection object inside the inspection object, processing the generated internal sectional image, and thereby inspecting an internal defect of the inspection object, wherein the image processing unit includes: a sectional image generation unit detecting the reflected echo generated from the flaw detector, processing the output signal, and generating the sectional image of the inside of the inspection object; a reference image generation unit generating a reference image that does not include a defect from the sectional image of the inside of the inspection object generated by the sectional image generation unit and generating a multi-value mask for masking a non-defective pixel from the obtained internal image of the inspection object; a feature amount computing unit calculating a defect accuracy by matching the brightness of the image of the inspection object obtained by the image acquisition unit and the reference image generated by the reference image generation unit; a defect detection processing unit detecting the defect by comparing the defect accuracy calculated by the feature amount computing unit with the multi-value mask generated by the reference image generation unit; and an output unit outputting the internal defect detected by the defect detection processing unit.

The present invention makes it possible to detect and output a fine defect near a normal pattern on an internal image of the inspection object including a mixture of aperiodic and complicated patterns.

Moreover, the present invention also makes it possible to detect the defect inside the inspection object by processing the sectional image of the inside of the inspection object detected using an ultrasonic wave.

These features and advantages of the invention will be apparent from the following more particular description of preferred embodiments of the invention, as illustrated in the accompanying drawings.

BRIEF DESCRIPTION OF THE DRAWINGS

FIG. 1 is an exemplary flow chart of a process showing a concept of a method for inspecting an internal defect of a wafer carrying various devices thereon according to a first embodiment of the present invention;

FIG. 5A is a sectional view of the multi-layer wafer showing a relation between the multi-layer wafer and an ultrasonic probe used as the inspection object in the first embodiment of the present invention;

FIG. 5B is a graph showing a reflected echo signal from the multi-layer wafer detected by using the ultrasonic probe used as the inspection object in the first embodiment of the present invention;

FIG. 8 is a block diagram showing a configuration of a defect detection unit of the ultrasonic inspection apparatus according to the first embodiment of the present invention;

DESCRIPTION OF THE PREFERRED EMBODIMENTS

Figure 2:
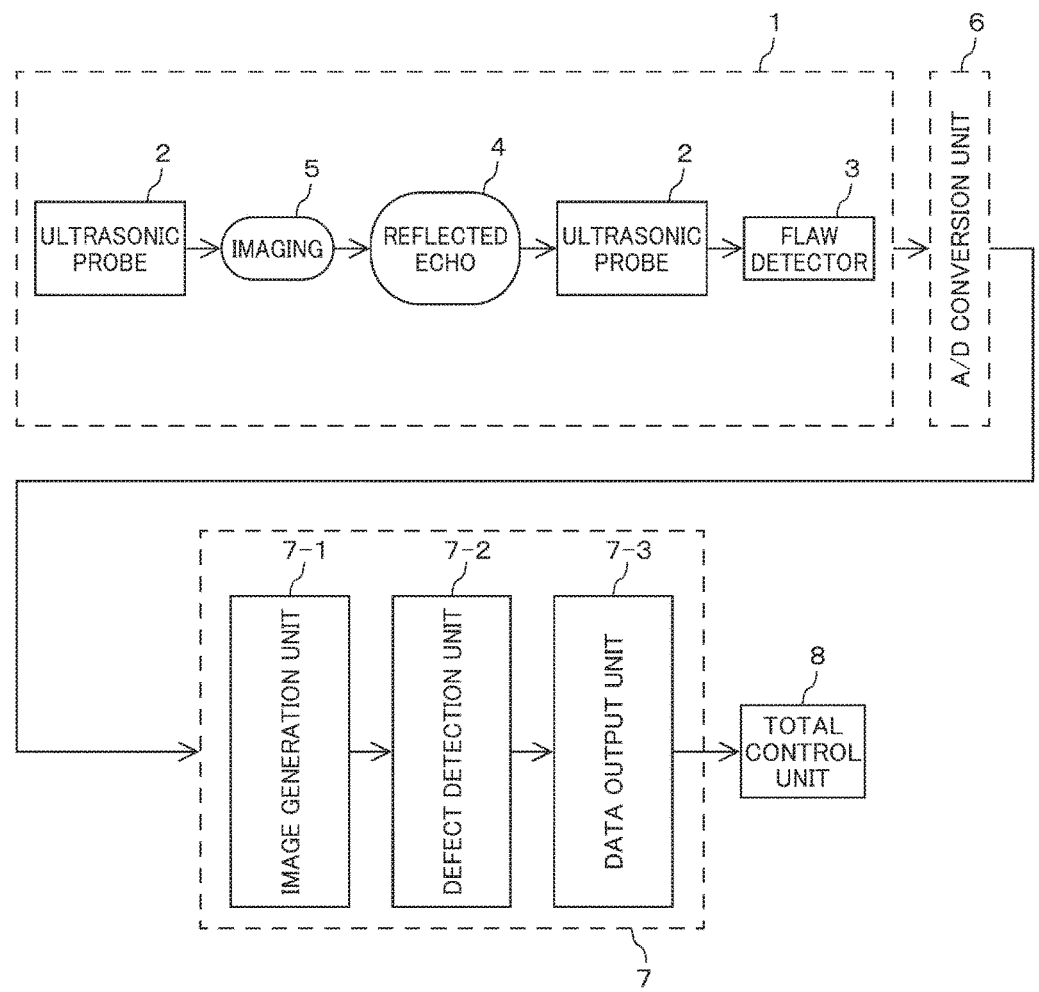
FIG. 2 is a block diagram showing a concept of an ultrasonic inspection apparatus according to the first embodiment of the present invention.

The present invention relates to a defect inspection method making it possible to separate signals of a normal pattern from that of a defect on an inspection object including an aperiodic pattern structure and thereby detecting a fine defect, and an apparatus for the same. That is, the present invention is configured to segment an image into regions each consisting of the same pattern group, group the regions, and detect a defect in a partial image of the same group, even if the image obtained from the inspection object includes an aperiodic pattern. The present invention is effective for an appearance inspection, a non-destructive inspection, and the like performed on such an inspection object having a complicated pattern structure.

Moreover, the present invention is configured to detect a defect in an internal image of the inspection object by segmenting an image into regions each consisting of the same pattern group, grouping the regions, and integrating features of the segmented internal images belonging to the group. Grouping is performed based on labels applied to segmented regions by a user in advance, or based on design data or an exposure recipe used when patterning each layer. Moreover, for detection of the defect, a reference segmented internal image is formed by integrating the features of the segmented internal images belonging to the same group, and the features are compared between the reference segmented internal image and each segmented internal image to calculate a defect accuracy. Furthermore, with respect to each pixel having a defect accuracy, a multi-value mask is generated from the segmented internal image, masking is performed on the pixel having the defect accuracy using the multi-value mask, and the remaining pixels are determined to be defective. By performing this on each group, the non-destructive inspection can be performed on the entire region of the inspection object covering a wide range.

Hereinbelow, embodiments of the present invention will be described with reference to drawings.

First Embodiment

Hereinbelow, an explanation of a case where a defect inspection method according to the present invention is applied to an ultrasonic inspection apparatus.

An implementation of the inspection method according to the present invention and the apparatus thereof is described with reference to FIGS. 1 to 14. First, an implementation of the ultrasonic inspection apparatus using a substrate having a multi-layer structure and a complicated pattern, such as a semiconductor wafer and a MEMS (Micro Electro Mechanical System) wafer, as the inspection object is described.

As a property of an ultrasonic wave, it propagates through the inspection object and, if there is a boundary at which a material property (acoustic impedance) changes, it is partially reflected. Since a large part of the ultrasonic wave is reflected when there is a cavity, such a defect as a void or a stripping can be detected with a high sensitivity based on the reflection intensity especially at a bonding surface of the wafer including multiple layers bonded together. Hereinbelow, a defect on the bonding surface of the multi-layer wafer is to be detected.

FIG. 2 is a conceptual diagram showing the implementation of the ultrasonic inspection apparatus according to the present invention. The ultrasonic inspection apparatus according to the present invention includes a detection unit 1, an A/D convertor 6, an image processing unit 7, and a total control unit 8.

The detection unit 1 includes an ultrasonic probe 2 and a flaw detector 3. The flaw detector 3 drives the ultrasonic probe 2 by applying a pulse signal to the ultrasonic probe 2. The ultrasonic probe 2 driven by the flaw detector 3 generates an ultrasonic wave and emits it toward the inspection object (sample 5). When the emitted ultrasonic wave enters the sample 5 having the multi-layer structure, a reflected echo 4 is generated from the surface of the sample 5 or from the bonding surface of the wafer. The reflected echo 4 is then received by the ultrasonic probe 2, processed by the flaw detector 3 as needed, and converted into a reflection intensity signal.

The reflection intensity signal is then converted into digital waveform data by the A/D convertor 6 and input to the image processing unit 7. The image processing unit 7 appropriately includes an image generation unit 7-1, a defect detection unit 7-2, and a data output unit 7-3. Signal conversion to be described later is performed by the image generation unit 7-1 on the waveform data input from the A/D convertor 6 to the image processing unit 7, thereby generating a sectional image of a specific bonding surface of the sample 5 from the digital waveform data. The defect detection unit 7-2 performs a process to be described later based on the sectional image of the bonding surface generated by the image generation unit 7-1 to detect the defect. The data output unit 7-3 generates data to be output as an inspection result such as information about an individual defect detected by the defect detection unit 7-2 and an image for observation of the section, and outputs the data to the total control unit 8.

Figure 3:
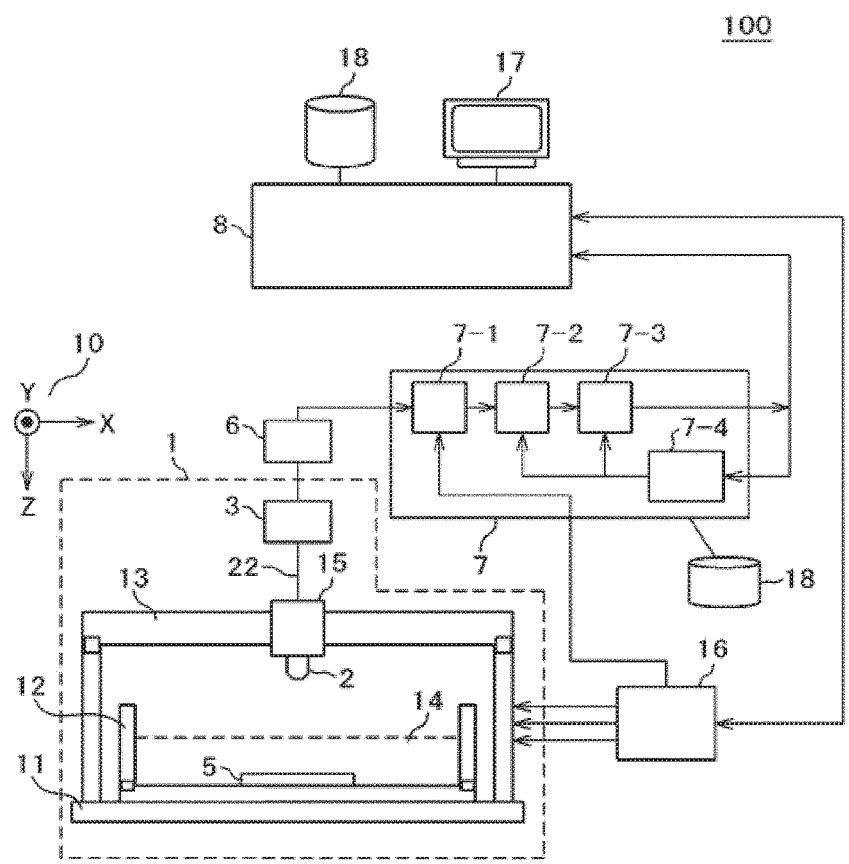
FIG. 3 is a block diagram showing a configuration of the ultrasonic inspection apparatus according to the first embodiment of the present invention.

Shown in FIG. 3 is a schematic diagram of an exemplary configuration of a specific ultrasonic inspection apparatus 100 implementing the configuration shown in FIG. 2. In FIG. 3, denoted by 10 is a coordinate system having three orthogonal axes of X, Y, and Z.

Reference numeral 1 in FIG. 3 corresponds to the detection unit 1 described with reference to FIG. 2. Denoted by 11 included in the detection unit 1 is a scanner table, 12 is a tank arranged on the scanner table 11, and 13 is a scanner arranged so as to bridge over the tank 12 on the scanner table 11 and movable in X, Y, and Z directions. The scanner table 11 is a base placed substantially horizontal. The tank 12 contains water 14 injected to the height indicated by a dotted line, and the sample 5 is placed on the bottom (in the water) of the tank 12. The sample 5 is the semiconductor wafer including the multi-layer structure and the like, as described above. The water 14 is a medium required for effectively propagating the ultrasonic wave emitted by the ultrasonic probe 2 into the sample 5. Denoted by 16 is a mechanical controller, which drives the scanner 13 in the X, Y, and Z directions.

For the sample 5, the ultrasonic probe 2 emits the ultrasonic wave from an ultrasonic output unit at its lower edge, and receives a reflected echo returned from the sample 5. The ultrasonic probe 2 is attached to a holder 15 and movable in the X, Y, and Z directions by the scanner 13 driven by the mechanical controller 16. Thus, the ultrasonic probe 2 can receive the reflected echo at a plurality of measurement points of the sample 5 set in advance while travelling in the X and Y directions, obtain a two-dimensional image of a bonding surface within a measurement range (X-Y plane), and thus inspect the defect. The ultrasonic probe 2 is connected to the flaw detector 3 that converts the reflected echo into a reflection intensity signal via a cable 22.

The ultrasonic inspection apparatus 100 further includes the A/D convertor 6 that converts the reflection intensity signal output from the flaw detector 3 of the detection unit 1 into a digital waveform, the image processing unit 7 that processes an image signal having been A/D converted by the A/D convertor 6, the total control unit 8 that controls the detection unit 1, the A/D convertor 6, and the image processing unit 7, and the mechanical controller 16.

The image processing unit 7 processes the image signal having been A/D converted by the A/D convertor 6 and detects an internal defect of the sample 5. The image processing unit 7 includes the image generation unit 7-1, the defect detection unit 7-2, the data output unit 7-3, and a parameter setting unit 7-4.

The image generation unit 7-1 generates an image from the digital data obtained by A/D converting the reflected echo returned from the sample surface and each bonding surface, and the like within the measurement range of the sample 5 set in advance and the position information of the ultrasonic probe obtained by the mechanical controller 16. The defect detection unit 7-2 processes the image generated by the image generation unit 7-1 and thereby becomes apparent or detects the internal defect. The data output unit 7-3 output the inspection result from becoming apparent or detecting the internal defect by the defect detection unit 7-2. The parameter setting unit 7-4 receives a parameter such as a measurement condition input from the outside, and sets the parameter to the defect detection unit 7-2 and the data output unit 7-3. In the image processing unit 7, for example, the parameter setting unit 7-4 is connected to a storage unit 18 that stores therein a database.

The total control unit 8 includes a CPU (incorporated in the total control unit 8) that performs various controls, receives the parameter or the like from the user, and appropriately connects a user interface unit (GUI unit) 17 that includes a display means for displaying information including an image of the defect detected by the image processing unit 7, the number of defects, a coordinate and dimension of the individual defect, and the like, and an input means, and the storage unit 18 storing therein the feature amount, image, and the like of the defect detected by the image processing unit 7. The mechanical controller 16 drives the scanner 13 based on a control instruction from the total control unit 8. It should be noted that the image processing unit 7, the flaw detector 3, and the like are also driven by the instruction from the total control unit 8.

Figure 4:
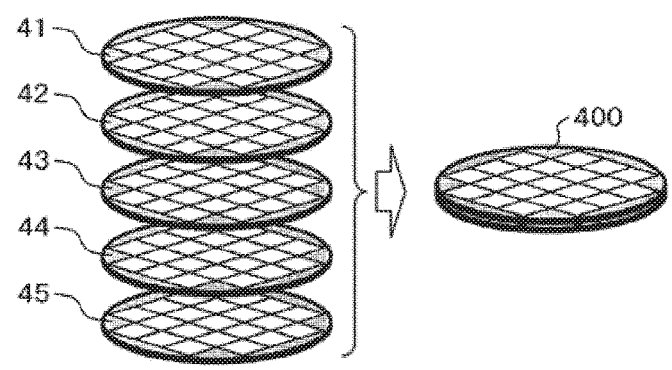
FIG. 4 is a perspective view of a wafer having a multi-layer structure used as an inspection object in the first embodiment of the present invention.

FIG. 4 shows a configuration of an inspection object 400 as an example of the sample 5. The inspection object 400 shown in FIG. 4 schematically represents appearance of a wafer including the multi-layer structure which is the main inspection object. The inspection object 400 is a laminated wafer formed by laminating and bonding wafers 41 to 45 of different types such as MEMS, CPU, memory, CMOS, and the like. The number of lamination is not limited to five but may be any number larger than one. The ultrasonic inspection apparatus 100 according to the present invention is used to inspect whether the wafers 41 to 45 in the inspection object 400 are properly bonded together on the whole lamination surface (bonding surface) without forming any depleted region such as a void or a stripping.

FIG. 5A is an example schematically showing a vertical structure of the inspection object 400 having the multi-layer structure shown in FIG. 4. When an ultrasonic wave 50 emitted from the ultrasonic probe 2 enters a surface 401 of the inspection object 400, the ultrasonic wave 50 transfers through the inspection object 400 and is reflected from the inspection object surface 401 and bonding surfaces 402, 403, 404, 405 between the wafers due to difference in acoustic impedance, and the ultrasonic probe 2 receives them as a single reflected echo.

A graph 51 in FIG. 5B shows an exemplary reflected echo from the inspection object received by the ultrasonic probe 2, with its abscissa representing time and ordinate representing reflection intensity. Time also indicates the depth of the inspection object 400. In the graph 51, by applying a visualization gate 52 (hereinbelow, simply referred to as "gate 52") to a time domain that may include the reflected echo from the bonding surface to be observed, the desired time domain is cut out and a peak value in the gate 52 is detected.

The image generation unit 7-1 of the image processing unit 7 detects the peak value in each scanning position from the reflected echo obtained while scanning the measurement range (X-Y plane) by the scanner 13 and converts the peak value into a gray value (for example, 0 to 255 in a case of generating a 256-tone image), thereby generating the sectional image of the bonding surface (an image of a section (a plane parallel to the wafer surface) in a depth direction from the wafer surface) from the gray value information at each scanning position.

Now, when the inspection object has the multi-layer structure like the inspection object 400 and has a plurality of bonding surfaces (such as 402 to 405) to be inspected, it is possible to set the gate 52 to the reflected echo in the time domain corresponding to each bonding surface and generate the sectional image of each bonding surface.

Figure 6A:
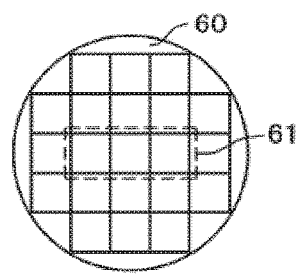
FIG. 6A is a plan view of the multi-layer wafer used as the inspection object in the first embodiment of the present invention.
Figure 6B:
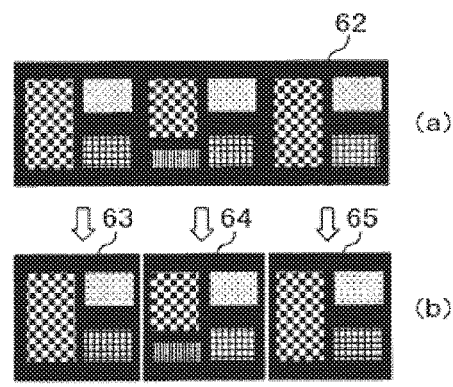
FIG. 6B is an image of the multi-layer wafer used as the inspection object in the first embodiment of the present invention.

Shown in FIGS. 6A and 6B are exemplary sectional images of the bonding surface generated. FIG. 6A schematically shows a top view of a laminated wafer 60 that is the inspection object. The laminated wafer 60 is eventually diced along straight lines shown in FIG. 6A to become a finished product. Hereinbelow, "chip" is used to refer to the diced product. Denoted by 62 in (a) of FIG. 6B is an exemplary sectional image of the bonding surface obtained from a region 61 delimited by a broken line and including three chips on the laminated wafer 60. Denoted by 63, 64, and 65 in (b) of FIG. 6B are partial sectional images made by segmenting the sectional image 62 in (a) of FIG. 6B into three regions corresponding to each chip. Since the partial sectional images 63 and 65 in (b) of FIG. 6B has the same devices mounted on the chip, the pattern configurations included in the obtained partial sectional image (hereinbelow, referred to as "pattern group") are also the same, while the left half of the partial sectional image 64 in (b) of FIG. 6B is constituted by two patterns, indicating that its pattern group is different from that of the partial sectional images 63 and 65.

According to this embodiment, for such an inspection object constituted by multiple types of chips having different pattern groups, the sectional images are grouped with respect to each region having the same pattern group (for example, the partial sectional images 63 and 65 belong to a group A and the partial sectional image 64 belong to a group B), and the defect detection process is performed with respect to each group.

FIG. 1 is the conceptual diagram of this case. Denoted by 101 is an appearance of a wafer including a mixture of various devices thereon as an example of the inspection object. The inspection object (wafer) 101 includes chips formed thereon in a grid shape, and the different hatch patterns indicate different types of the devices constituting the chip. In other words, basically the inspection images constituted by the same pattern group are obtained from the regions of the same hatch pattern.

In the defection inspection according to the invention, the detection unit 1 obtains a surface image or an internal sectional image of the inspection object 101 (S11), and the image processing unit 7 first extracts partial images constituted by the same pattern group from the obtained surface image or the internal sectional image of the inspection object 101 (S12). The partial images corresponding to the regions 103, 104 of the wave hatch pattern in the inspection object 101 are extracted from the extracted partial image and aligned as shown by 102 (S13). The image alignment means, because the extracted partial image 103 to 108 have the same pattern group, performing a position correction so that regions of the same pattern may be present at the same coordinate value in each image.

Features are then calculated in each pixel of each image and integrated between images as denoted by 109 and 110 (S14). This step is performed on all the pixels in the partial images to generate a reference partial image 111 (S15) and generate a multi-value mask 112 (S16). Integral comparison (S17) with the generated reference partial image 111 and the multi-value mask 112 is then performed on each of the partial image 103 to 108 to detect a defect 113. Finally, the detected defect 113 is combined on the wafer level (S18) and the result is displayed (S19). The same process is performed on the partial images constituted by other pattern groups (images corresponding to the striped, dotted, or checkerboard hatch patterns on the wafer 101).

Figure 7:
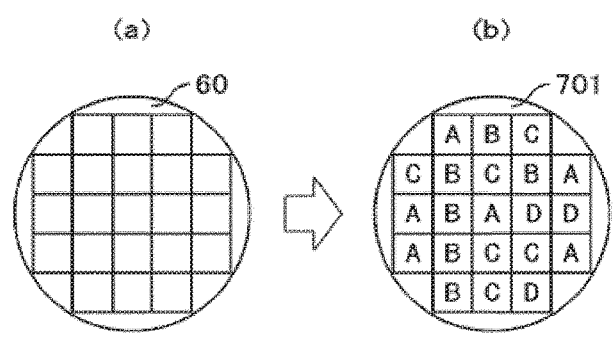
FIG. 7 is a plan view of the wafer with a label applied to each chip of the multi-layer wafer used as the inspection object in the first embodiment of the present invention.

Here, extracting the partial images having the same pattern group from the inspection object (wafer) 101 used as the inspection object at Step S12 is performed by receiving a prior setting from the user. FIG. 7 shows an example thereof. Denoted by 60 in (a) of FIG. 7 is a layout of chips formed on the wafer 101 used as the inspection object. This is displayed on a screen by the user interface unit 17 shown in FIG. 3, and the parameter setting unit 7-4 receives the labels applied to the individual chip on the screen by the user. In this process, the inspection object 101 is grouped based on the labels applied by the user.

Denoted by 701 in (b) of FIG. 7 is an example of the result, which is formed by segmenting the wafer 101 used as the inspection object into partial images in the unit of chips and grouping the partial images into four categories of A to D based on the labels applied by the user. An automatic setting is also possible using the recipe for the exposure even if there is no user setting. The exposure recipe includes exposure position information indicative of where to print a circuit pattern on the substrate, exposure order, and the like, from which the information about the pattern to be formed at each position can be obtained.

Next, a configuration of the process performed by the defect detection unit 7-2 of the image processing unit 7 is described. FIG. 8 shows an example thereof. The defect detection process is performed using the partial images constituted by the same pattern group. An inspection recipe 801 constituted by various parameter values used for the processing, and an image of the wafer whole surface 802 are input. The defect detection unit 7-2 generally includes a partial image group generation unit 81, a reference image generation unit 82, a defect detection processing unit 83, and a defect information output unit 84. First, when the wafer whole surface 802 is input to the defect detection unit 7-2, a plurality of partial images applied with the same label by the partial image group generation unit 81 (for example, 103 to 108 in FIG. 1) are input to the reference image generation unit 82. The reference image generation unit 82 generates a reference partial image 804 and a multi-value mask 805. The reference partial image 804 means the normal image constituted by the same pattern group as that of the input partial image.

Figure 9A:
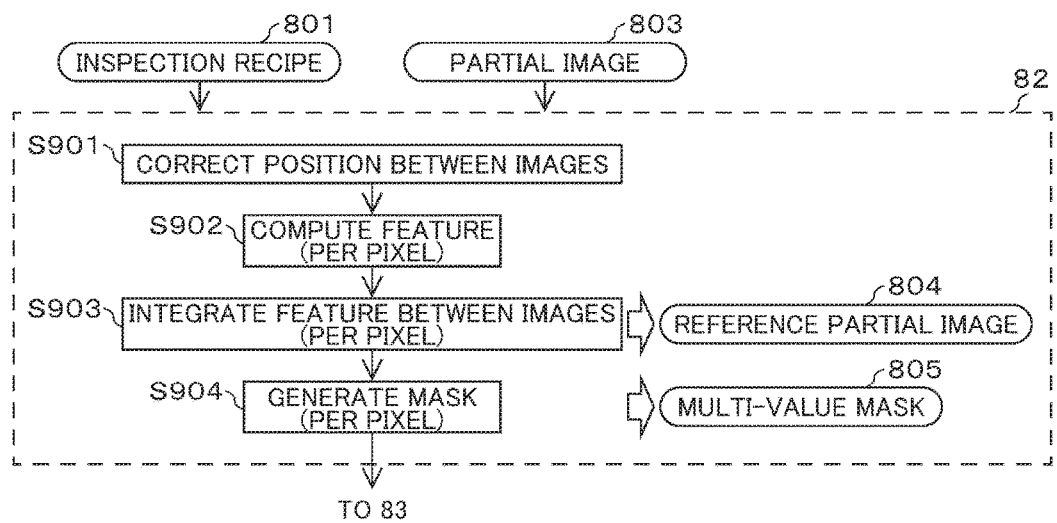
FIG. 9A is a block diagram showing a configuration of a reference image generation unit of the ultrasonic inspection apparatus according to the first embodiment of the present invention.
Figure 9B:
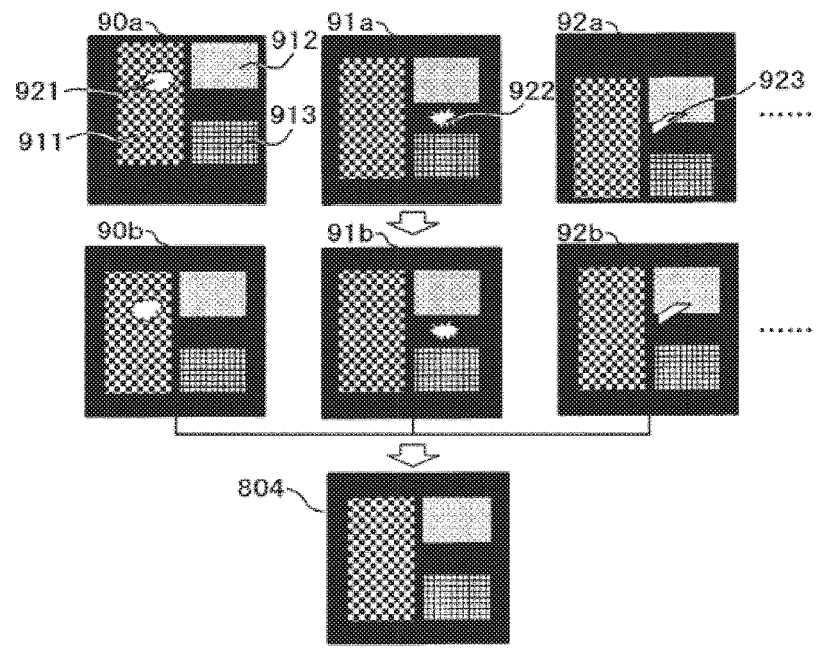
FIG. 9B is a process flow chart of the reference image generation unit in the defect detection unit of the ultrasonic inspection apparatus according to the first embodiment of the present invention.

Shown in FIGS. 9A and 9B is an example of a method of generating the reference partial image. Denoted by 90a, 91a, 92a, . . . in FIG. 9B are the partial images of the same label cut out of the inspection object 101. These partial images include the same pattern group (denoted herein by three different hatch patterns 911 to 913). The defects 921 to 923 (indicated by white color) may possibly be included. There also may be a positional shift of the pattern due to a slight difference in the position of obtaining the image when scanning (sampling error) (indicated by difference in positions of the hatch patterns 911 to 913 with respect to the black background). Thus, correction of the position of each image, namely inter-image position correction is performed so as to correct the position of the partial image, or so as to align the coordinates of the hatch patterns 911 to 913 with the black background (S901).

The position correction between the partial images at Step S901 is performed using a general matching method such as: specifying one partial image; calculating a shift amount that makes the minimum sum of squares of the luminance difference between the specified image and other partial images to be corrected while shifting the partial image to be corrected with respect to the specified image, or calculating a shift amount that makes the maximum normalized cross-correlation coefficient; and shifting the partial image by the calculated shift amount. Denoted by 90b, 91b, 92b, . . . in FIG. 9B are the partial images after the position correction.

The features of the pixels in the partial images 90b, 91b, 92b, . . . after the position correction are then calculated (S902). The feature may be any of a contrast in each pixel (Equation 1) (luminance gradient with peripheral pixels), a luminance average including proximate pixels (Equation 2), a luminance dispersion value (Equation 3), increase or decrease of the brightness and its maximum gradient direction with respect to the proximate pixels, which represents the feature of the pixel.

[Equation 1]

$$F1(x,y); \max\{f(x,y), f(x+1,y), f(x,y+1), f(x+1,y+1)\} - \min\{f(x,y), f(x+1,y), f(x,y+1), f(x+1,y+1)\} \quad \text{(Equation 1)}$$

[Equation 2]

$$F2(x,y); \Sigma f(x+i,y+j)/M \quad \text{(Equation 2)}$$

$(i, j=-1, 0, 1\ M=9)$

[Equation 3]

$$F3(x,y); [\Sigma\{f(x+i,y+j)^2\} - \{\Sigma f(x+i,y+j)\}^2/M]/(M-1) \quad \text{(Equation 3)}$$

$i, j=-1, 0, 1\ M=9$ where f(x, y) is the luminance value of the coordinate (x, y) in the partial image.

Next, as described above, the feature of each pixel (x, y) calculated for each partial image is integrated between the partial images (S903) to generate the reference partial image 804. One example of this processing method includes: collecting features Fi(x, y) of the corresponding coordinate (x, y) between partial images (i is the number designated to the partial image), and thereby statistically determining the reference feature value S(x, y) of the feature of each pixel as represented by Equation 4. The luminance value of the partial image equal to the reference feature value is determined as the luminance value of the reference partial image. In this manner, the reference partial image 804 exclusive of influences from a defect is generated.

[Equation 4]

$$S(x,y) = \text{Median}\{F1(x,y), F2(x,y), F3(x,y), \ldots\} \quad \text{(Equation 4)}$$

Median: Function outputting a median value (median) of the feature of each partial image S(x, y): Reference feature value F* (x, y): Feature value of the partial images 90b, 91b, 92b, . . . after position correction It is noted that, as represented by Equation 5, the statistical processing may be performed by calculating an average of the feature at the corresponding coordinate between images and using the luminance value of the partial image having its feature closest to the average as the luminance value of the reference partial image.

[Equation 5]

$$S(x,y) = \Sigma\{F_i(x,y)\}/N \quad \text{(Equation 5)}$$

i: the number designated to the partial image
N: partial image

Figure 10:
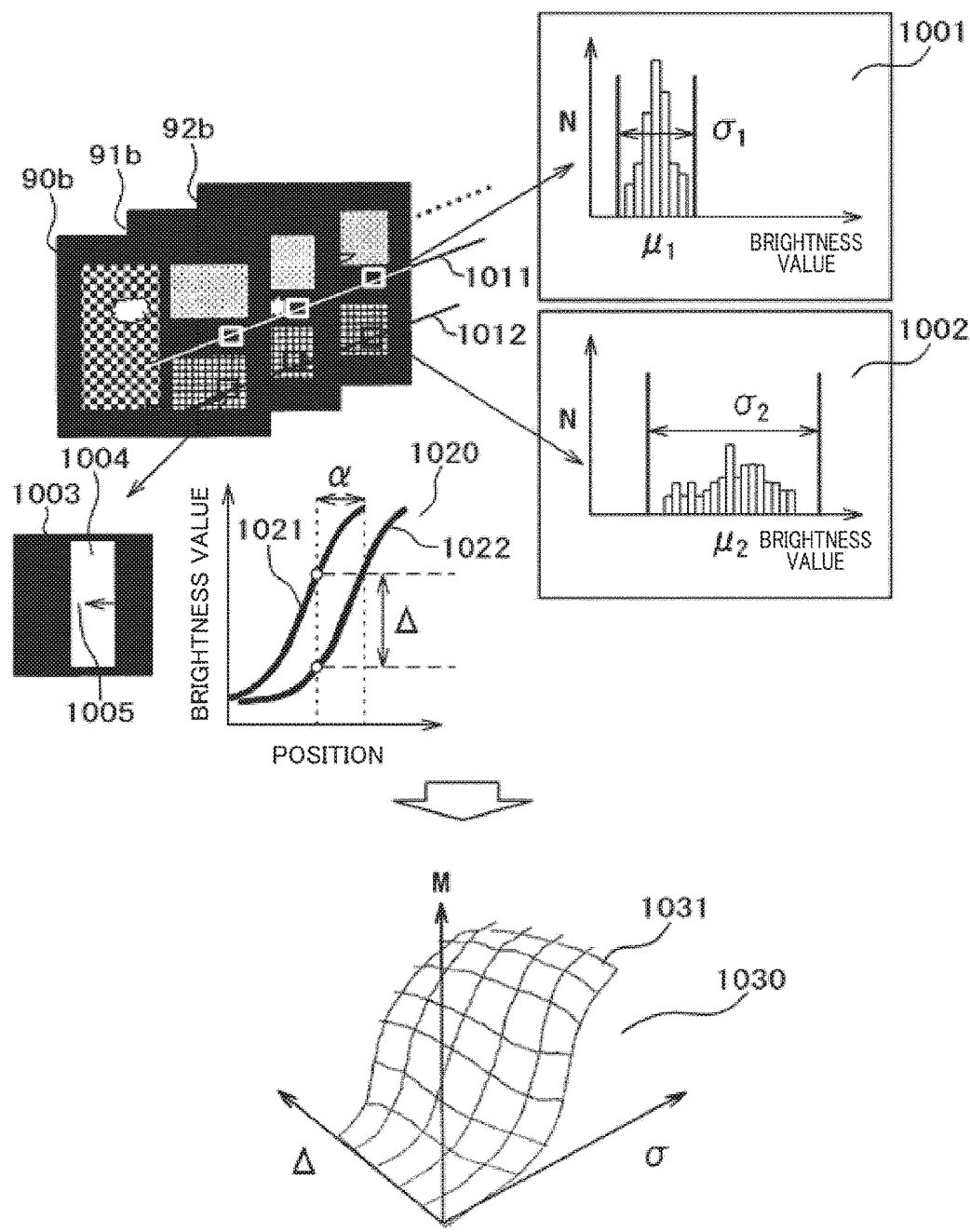
FIG. 10 shows an image and a graph showing a procedure of generating a multi-value mask by the defect detection unit of the ultrasonic inspection apparatus according to the first embodiment of the present invention.

As shown in FIG. 8, the reference image generation unit 82 generates, in addition to the reference partial image, the multi-value mask 805 for eliminating (masking) a non-defective pixel between images. One example of the generation procedure is shown in FIG. 10. The multi-value mask according to this embodiment is set by calculating multiple values (0 to 255) with respect to each pixel in the image. For the partial images 90b, 91b, 92b, . . . after the position correction shown in FIG. 9B, the luminance value f(x, y) of the corresponding pixel is integrated, and the dispersion value of the luminance values is calculated as the feature according to Equation 6.

In FIG. 10, a graph 1001 shows a distribution of luminance values of a coordinate indicated by a white square 1011 in the partial images 90b, 91b, 92b, . . . , showing that the dispersion value σ1 is calculated by integrating the luminance values between the images. A graph 1002 shows the distribution of the luminance values of the coordinate indicated by a black square 1012 in the partial images 90b, 91b, 92b, . . . , showing that the dispersion value σ2 is calculated by integrating the luminance values between the images. The dispersion value σ is calculated for all the pixels within the partial images in the same manner.

Another feature is also calculated from the same pixel. Reference numeral 1003 shows a pattern near the coordinate indicated by the black square 1012. There is a longitudinal pattern 1004 with high luminance. A curve 1021 in the graph 1020 shows a luminance profile of a location indicated by an arrow 1005 (→ ←) on the longitudinal pattern 1004 in the pattern 1003. A curve 1022 shows a luminance profile when the longitudinal pattern 1004 in the pattern 1003 is shifted by an amount α. Thus, Δ in the graph 1020 indicates the luminance difference caused by the positional shift by the amount α. The Δ is regarded as the second feature of the pixel indicated by the black square 1012. The luminance difference Δ is calculated for all the pixels within the partial images in the same manner. Then, based on the values of the two features σ and Δ calculated from all the pixels within the partial images, a multi-value mask value M is calculated according to Equation 7. An aspect 1031 in the three-dimensional graph 1030 corresponds to the value M of the multi-value mask calculated from Δ and σ.

[Equation 6]

$$\sigma(x,y) = [\Sigma\{f_i(x,y)^2\} - \{\Sigma f_i(x,y)\}^2/N]/(N-1) \quad \text{(Equation 6)}$$

i: the number designated to the partial image
N: partial image

[Equation 7]

$$M(x,y) = k \times \sigma(x,y) + m \times \Delta(x,y) + n \quad \text{(Equation 7)}$$

Since σ and Δ are calculated from the features of each pixel, the value M of the multi-value mask is calculated separately with respect to each pixel according to σ and Δ. This may cause a difference in the pattern luminance values between partial images, despite the same pattern group, due to a fabrication tolerance or a sampling error at the time of image acquisition, and the difference is reflected on the mask.

The parameters α (described in FIG. 10), k, m, and n are set in advance, and the distribution of the multi-value mask M indicated by the aspect 1031 in the three-dimensional graph 1030 can be adjusted by adjusting these parameters. In addition, although the example was given in which the multi-value mask M was calculated based on σ and Δ calculated by integrating the features of each pixel between the partial images, any feature indicative of the property of the pixel can be used, and the way of integrating the feature may also be changed accordingly. Furthermore, the number of the features to be integrated is not limited to two but the multi-value mask M can be calculated from any number more than one of the integration features. Although the value of n was described as a fixed value, it can be set with respect to each pixel in the partial image.

Although the above description was given taking an example of generating the reference partial image exclusive of any defect from partial images, the reference image may also be generated by cutting out partial images constituted by the same pattern group from a good sample guaranteed to be free of defect.

Hereinbelow, the defect detection processing unit 83 that detects a defect from the partial images 103 to 108 is described using the reference partial image 804 and the multi-value mask 805 in FIG. 8.

Figure 11:
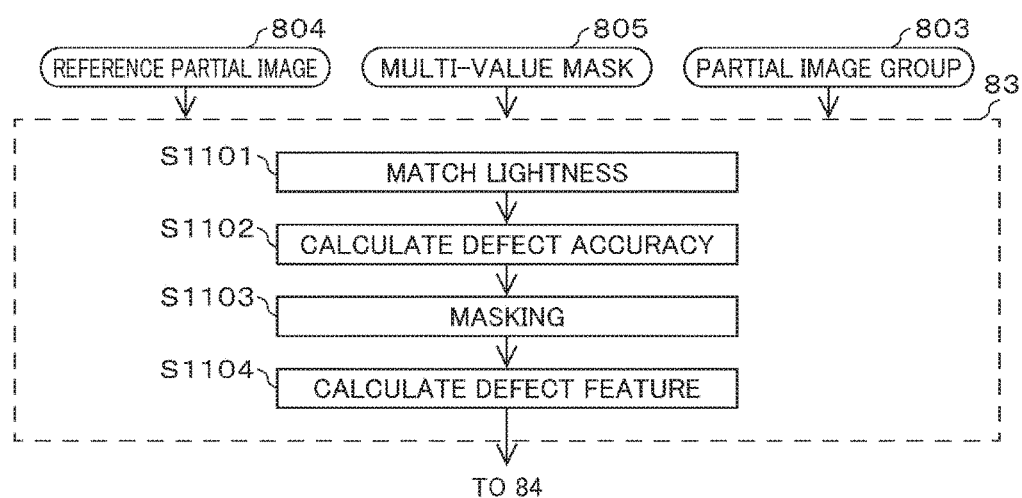
FIG. 11 is a flow chart showing a defect detection process by the defect detection unit of the ultrasonic inspection apparatus according to the first embodiment of the present invention.

FIG. 11 shows an example of the process performed by the defect detection processing unit 83. The reference partial image 804 and the multi-value mask 805 output from the reference image generation unit 82 and a partial image group 803 of the inspection object (partial images in the same group) are input, which images have been subjected to an inter-image position correction, as described with reference to FIG. 9.

First, each image in the partial image group used as the inspection object is matched with the reference partial image for the brightness, as needed (S1101). There may be difference in brightness even between the partial images constituted by the same pattern group, due to difference in thickness of each layer when the sample is formed of a multi-layer film, or due to warpage of a wafer when the inspection object is the wafer. Therefore, matching of the brightness is performed (correct the brightness of one image so that they have the same brightness).

One example of the method thereof described herein includes the step of correcting the brightness of the partial image to match that of the reference partial image 804 based on the least squares approximation. Assuming that there is a linear relation represented by Equation 8 between the pixels f(x, y) and g(x, y) of the respective image in the partial image group 803 and the reference partial image 804, a and b are calculated so that Equation 9 makes the minimum value and they are used as correction coefficients "gain" and "offset". The brightness is corrected on the corresponding pixels in respective images in the partial image group 803 and the reference partial image 804 as well as all the pixel values f(x, y) in the partial images to be corrected for the brightness, as represented by Equation 10

[Equation 8]

$$g(x,y) = a + b \cdot f(x,y) \quad \text{(Equation 8)}$$

[Equation 9]

$$\Sigma\{g(x,y) - (a + b \cdot f(x,y))\}^2 \quad \text{(Equation 9)}$$

[Equation 10]

$$f'(x,y) = \text{gain} \cdot f(x,y) + \text{offset} \quad \text{(Equation 10)}$$

The defect accuracy is then calculated for each pixel in a partial image 1110 (S1102). An exemplary defect accuracy is defined by a value indicative of an appearance at the normal time, namely a degree of deviation from the luminance value of the reference partial image 804, which is calculated according to Equation 11.

[Equation 11]

$$d(x,y) = f'(x,y) - g(x,y) \quad \text{(Equation 11)}$$

The masking process is performed on the defect accuracy calculated according to Equation 11 using the multi-value mask 805 for each pixel, and the remaining pixels are detected as defective (S1103).

The masking process detects the defect when the defect accuracy exceeds a mask value as represented by Equation 12.

[Equation 12]

$$P(x,y): \text{defect (if } d(x,y) \geq M(x,y))$$

$$P(x,y): \text{normal (if } d(x,y)9 < M(x,y)) \quad \text{(Equation 12)}$$

where, $m(x, y) = k \times \sigma(x, y) + m \times \Delta(x, y) + n(x,y)$

It is noted that, although the example of detecting the defect by masking the pixels brighter than the luminance value of the reference partial image 804 is described above, the same applied to the pixels darker than the luminance value of the reference partial image 804. As already described, an influence by the fabrication tolerance and the sampling error at the time of image acquisition between the images is taken into account for the multi-value mask 805. Thus, the multi-value mask 805 can mask the pixels including a noise of the fabrication tolerance or the sampling error in the defect accuracy calculated according to Equation 11.

Finally, the defect feature of a defective pixel is calculated for determining whether it is defective or not (S1104). There may be one or more defect features indicative of the feature of the defect. Examples include an area, a maximum length, a luminance value, an edge intensity, and the like of the defect.

The process steps S1101 to S1104 by the defect detection processing unit 83 described above are performed on the partial images constituted by the same pattern group after grouping, and the same is performed on each group.

As described above, the information about the defect detected by the process per group is then rearranged into a chip array on the inspection object by the defect information output unit 84. Its concept is shown in FIGS. 12A and 12B.

Figure 12A:
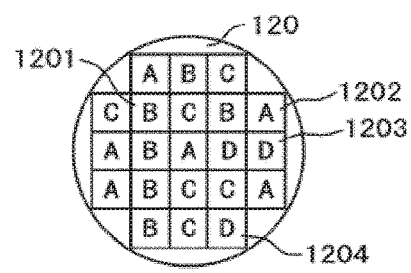
FIG. 12A is a plan view of the wafer labeled with respect to each pattern group according to the first embodiment of the present invention.

A wafer 120 shown in FIG. 12A is an inspection object segmented into regions constituted by the same pattern group and labeled. Based on this, it is assumed that the defect detection process is performed on each of the groups A to D to detect a defect 1202a in a region 1202 of the group A, a defect 1201a in a region 1201 of the group B, a defect 1203a in a region 1203 of a group C, and a defect 1204a in a region 1204 of a group D, as shown in FIG. 12B.

Upon receipt of this result, the defect information output unit 84 in FIG. 8 rearranges the output result from the segmented partial images based on region arrangement information of the inspection object (wafer) 120. That is, it maps the detected results 1201a to 1204a at the positions of regions 1201 to 1204 in FIG. 8B, generates a defect distribution image 121 on the wafer, and output the defect distribution image 121. The defects at 1202a and 1203a detected in separate processes are thus output as a single defect. At the same time, the coordinate indicative of the defect position in the partial image is converted into the coordinate system of the inspection object 101, and separately calculated defect features (area, maximum length, etc.) are also integrated. The defect information after the conversion and integration is output to the data output unit 7-3 and displayed by a display means such as a display unit via the user interface unit (GUI unit) 17. It is also possible to simultaneously determining whether the chip is good or defective based on the defect features and display the result. For example, the number of defects, the maximum defective area, the ratio of the defective pixels in the chip are measured, and the chip exceeding a judgement condition input as the inspection recipe is output and displayed as a faulty chip.

Figure 12B:
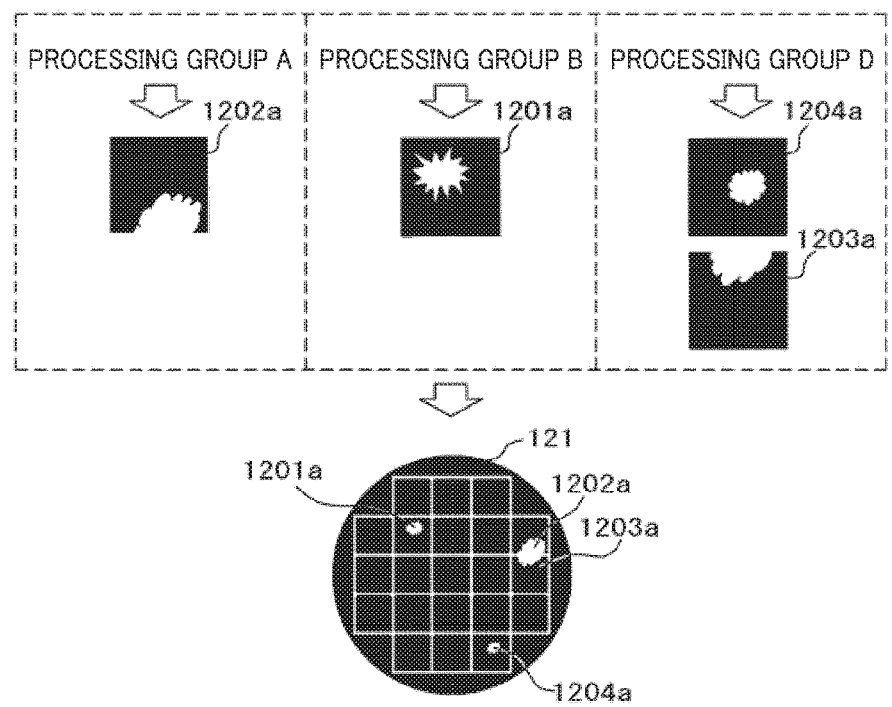
FIG. 12B is a plan view of chips on the wafer showing an example in which information of the defect detected with respect to each group is integrated and output by a defect information output unit in the defect detection unit of the ultrasonic inspection apparatus according to the first embodiment of the present invention.
Figure 12C:
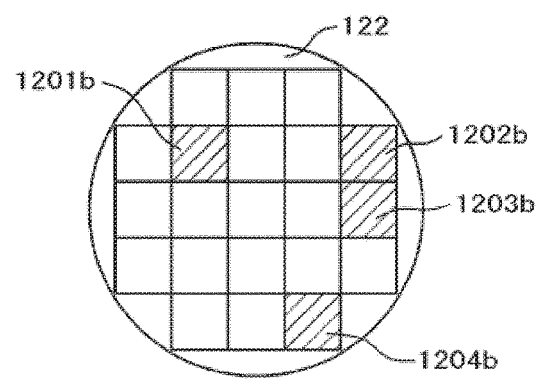
FIG. 12C is a plan view of the wafer showing another example in which information of the defect detected with respect to each group is integrated and output by a defect information output unit in the defect detection unit of the ultrasonic inspection apparatus according to the first embodiment of the present invention.

Although FIG. 12B shows an example of mapping the detected result and outputting the defect distribution image on the wafer as denoted by 121, it is also possible to display the defective chips in a color different from that of defect-free chips on the wafer, as shown in FIG. 12C.

Figure 13A:
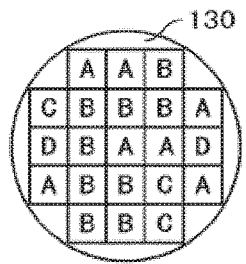
FIG. 13A is a plan view of the wafer labeled with respect to each pattern group according to the first embodiment of the present invention.
Figure 13B:
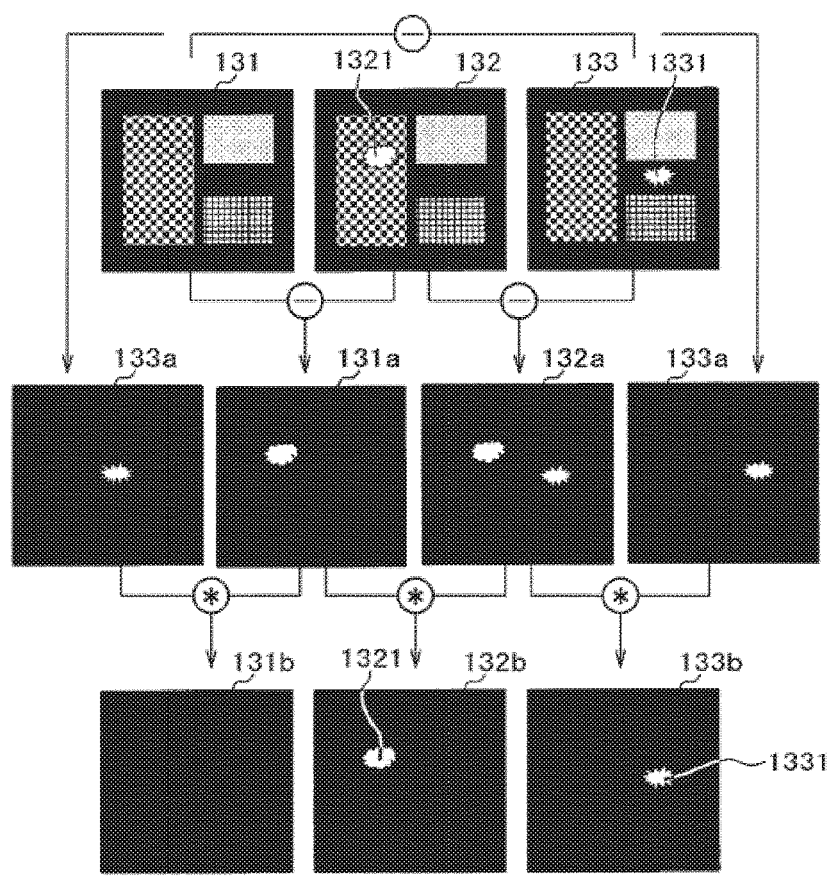
FIG. 13B is a flow chart showing a process by the defect detection unit of the ultrasonic inspection apparatus according to the first embodiment of the present invention but different from what is described with reference to FIG. 12B.

For inspecting the wafer, the defect detection process also has a plurality of detection methods other than using the luminance difference compared with the reference image as the defect accuracy, as described above. Its concept is shown in FIGS. 13A and 13B. FIG. 13A shows an wafer 130 used as the inspection object segmented into regions constituted by the same pattern group and labeled. In this example, the group A includes seven regions, the group B includes nine regions, the group C includes three regions, and the group D includes two regions.

The defect detection process according to this embodiment can change the method of detecting the defect depending on the number of the regions having the same label. For example, as described above, the reference partial image with the influence by the defect removed is statistically generated by integrating the features of each partial image. However, as the number of the partial images decrease, reliability of the statistical processing decreases. Therefore when the number of the regions is smaller than a certain number (for example, less than four regions), the statistical processing is not performed, but comparison between actual subjects, comparison with a model, comparison with a fixed threshold, and the like may be performed. An exemplary processing in the case of three partial images like the group C is as follows.

Denoted by 131, 132, 133 in FIG. 13B are partial images generated by cutting out the regions corresponding to the label C in the inspection object (wafer) 130 and performing position correction and brightness matching, where the partial images (hereinbelow, referred to simply as images) 132 and 133 include defects 1321 and 1331, respectively. For these three images, differences among them (difference image: absolute value here) are computed. A difference image 131a takes a difference between the images 131 and 132, a difference image 132a takes a difference between the images 132 and 133, and a difference image 133a takes a difference between the images 133 and 131. The defective portion becomes apparent. Furthermore, the defect accuracy is calculated by taking the minimum value from the differences between two images. That is, a difference image 131b is the minimum value between the difference image 133a and the difference image 131a, a difference image 132b is the minimum value between the difference image 131a and the difference image 132a, and a difference image 133b is the minimum value between the difference image 132a and the difference image 133a; the difference image 131b is the defect accuracy of the image 131, the difference image 132b is the defect accuracy of the image 132, and the difference image 133b is the defect accuracy of the image 133. The defects 1321 and 1331 are detected by masking them with the fixed value or the multi-value mask.

As another example of processing, when there are two or less partial images like the group D, it is also possible to detect the defect by performing a processing similar to that shown in FIG. 11 using the reference partial image extracted from a good sample as an input. It is also possible as another example to detect the defect regarding the luminance value itself in an unmasked area as the defect accuracy using a binary mask that can fully mask a non-inspection area (designed in advance), based on a given threshold.

As described above, this embodiment is characterized in detecting the defect with respect to each group by grouping the whole regions of the inspection object to each pattern group constituting the region. This enables detection of the defect with a high accuracy even on a wafer not constituted by regular pattern groups. Furthermore, it is also effective for the case in which the same inspection object is a multi-layer bonded wafer, especially with each layer having irregular pattern groups.

Figure 14:
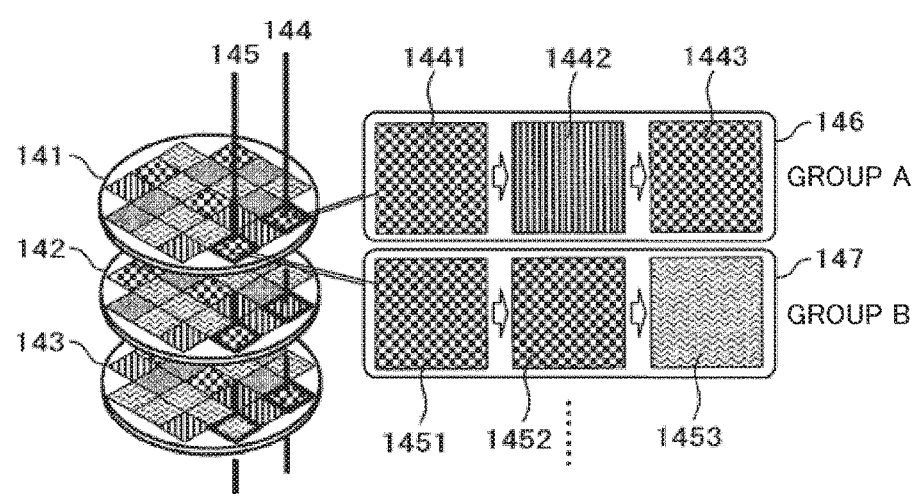
FIG. 14 shows a perspective view of the wafer and an image of chips showing an example of grouping on the multi-layer wafer used as the inspection object according to the first embodiment of the present invention.

Reference numerals 141, 142, 143 in FIG. 14 schematically show arrays of each layer in a three-layer bonded wafer used as the inspection object. Each layer of the wafer is constituted by chips having a plurality of different pattern groups (indicated by different hatch patterns).

When viewing the chips on the wafer in the depth direction, the combinations of the pattern groups (group A146 and group B147) are different. Lines 144, 145 in FIG. 14 indicate the chips superimposed in the depth direction. On the first layer of the wafer 141, the same patterns are formed on a chip 1441 on the line 144 and a chip 1451 on the line 145, while the patterns formed on a pattern 1442 on the line 144 and a pattern 1452 on the line 145 on the second layer of the wafer 142 are different and the patterns formed on a pattern 1443 on the line 144 and a pattern 1453 on the line 145 on the third layer of the wafer 143 are also different. In such a case, it is possible to use grouping information of any one of the wafers 141 to 143 depending on where the bonding surface to be inspect is located, and it is also possible to generate combined grouping information of the these wafers to be commonly used for all the bonding surfaces.

The group A146 and the group B147 in FIG. 14 show the label information of each chip when the chips on the lines 144 and 145 are superimposed in the depth direction. The label information may be newly grouped depending on the difference of the label combination designating the region having the chip combination with the same pattern as the chip pattern on the line 144 formed thereon as a label A and the region having the chip combination with the same pattern as the chip pattern on the line 145 as a label B, and it is stored as the label information uniquely determined for the bonded wafer. The label information is automatically set according to the combination pattern in the depth direction based on the label information of each layer of the wafer.

According to this embodiment, even though the image obtained from the inspection object includes aperiodic patterns, the image is segmented and grouped into regions having the same pattern group and a defection is detected within the partial images belonging to the same group. Thus, even when the image obtained from the inspection object includes such aperiodic patterns, it is possible to segment and group such an image into the regions having the same pattern group and detect the defect within the partial images belonging to the same group.

Second Embodiment

The implementation of the inspection method according to the present invention and the apparatus thereof is described above taking an example of a substrate having a multi-layer structure and a complicated pattern such as a semiconductor wafer and a MEMS (Micro Electro Mechanical) wafer as the inspection object, and it is also applicable to an inspection of an IC package mounted on an IC tray or the like.

Figure 15A:
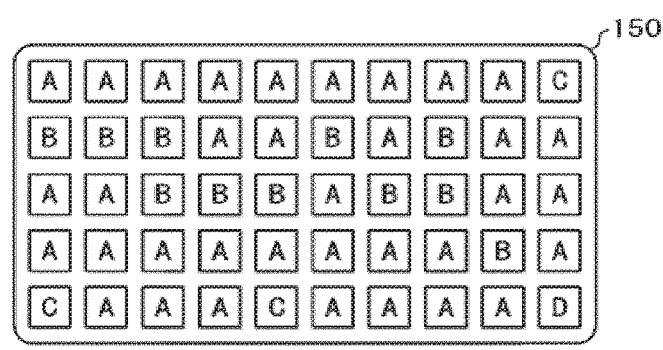
FIG. 15A is a plan view of an IC tray used as an inspection object according to a second embodiment of the present invention.
Figure 15B:
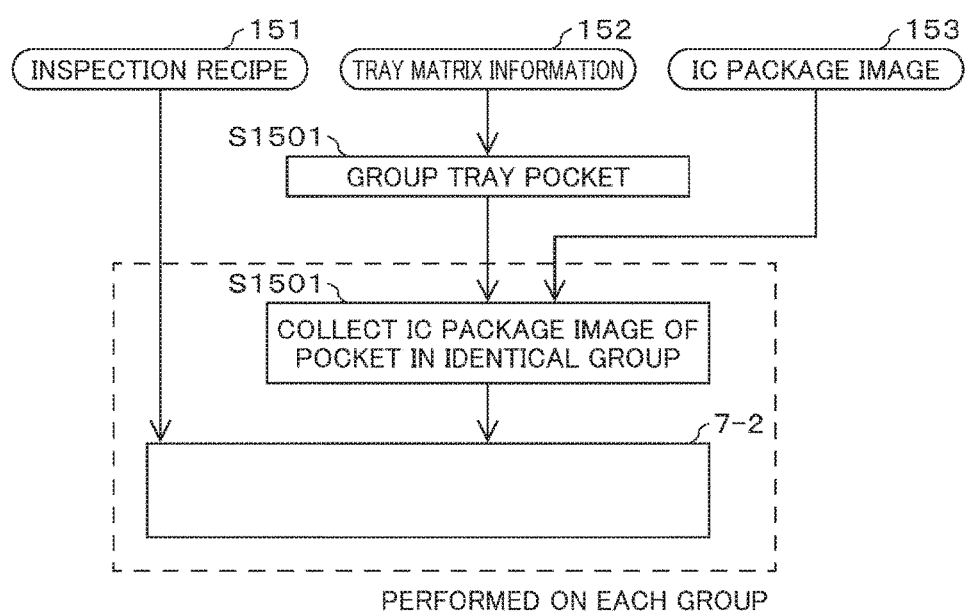
FIG. 15B is a flow chart showing a process for the IC tray used as the inspection object according to the second embodiment of the present invention.

One example is shown in FIGS. 15A and 15B. Denoted by 150 in FIG. 15A is an IC tray, and labels A, B, C, and D in each pocket of the IC tray 150 indicate different types and model numbers of the IC packages placed in the IC tray. FIG. 15B shows a processing procedure according to this embodiment. With the inspection method of the present invention and the apparatus thereof, tray matrix information 152 of the IC package including the type and the model number (model number of IC package placed in each pocket on the tray, and the like) is received along with an inspection recipe 151, tray pockets are grouped based on the tray matrix information 152 (S1500), images of the pockets belonging to the same group are collected from images 153 of the IC packages on the tray pockets obtained (S1501), and the defect detection process described with reference to FIG. 8 in the first embodiment is performed at the defect detection unit 7-2. The same process is performed on each group. This enables a highly sensitive inspection even when multiple types of IC packages are placed on a single IC tray.

The above processing is also effective for the inspection of the IC package formed on a strip substrate. Instead of labeling each pocket on the IC tray, labels may be applied according to the type of the device placed therein or the pattern group of the obtained image, and the same processing is applied thereafter.

Embodiments of the present invention are described above taking an example of the defect inspection using the ultrasonic inspection apparatus in a case where there are multiple types of devices formed on a wafer or an IC tray, but it is also effective for an inspection of a discrete IC package. In this case, the reference image is generated from a good sample with respect to each type in advance;

the corresponding reference image is input according to the type of the inspection object; and the defect accuracy is calculated to make a determination. When there is only one type of constructions formed on the wafer or IC packages placed on the IC tray and the obtained image of the inspection object is constituted by a regular pattern, the present inspection method can be used by applying the same labels to all the regions.

The present invention is applicable not only to images obtained by the ultrasonic inspection apparatus but also to non-destructive inspection images obtained by an x-ray defect inspection apparatus and images of appearance inspection.

The present invention has been specifically described above based on its embodiments, and it is obvious that the present invention is not limited to the embodiments and various modifications can be made without departing from the spirit of the invention.

The invention may be embodied in other specific forms without departing from the spirit or essential characteristics thereof. The present embodiment is therefore to be considered in all respects as illustrative and not restrictive, the scope of the invention being indicated by the appended claims, rather than by the foregoing description, and all changes which come within the meaning and range of equivalency of the claims are therefore intended to be embraced therein.

The invention claimed is:

1. A defect inspection method for a defect inspection apparatus having a tank and an ultrasonic probe, the method comprising the steps of:
   placing a wafer on a bottom of the tank, the bottom of the tank being filled with a medium, the medium being capable of propagating an ultrasonic wave;
   obtaining an image of the wafer having patterns formed thereon, by
   (1) sending the ultrasonic wave to the wafer while scanning a plane parallel to a surface of the wafer with the ultrasonic probe;
   (2) receiving a reflected echo wave returned from the wafer to which the ultrasonic wave was sent using the ultrasonic probe; and
   (3) generating an image of the plane parallel to the surface of the wafer from the received reflected echo wave;
   generating a reference image that does not include a defect from the obtained image of the wafer;
   generating a multi-value mask for masking a non-defective pixel from the obtained image of the wafer;
   calculating a defect accuracy by matching the brightness of the obtained image of the wafer and the reference image; and
   detecting a defect by comparing the calculated defect accuracy with the generated multi-value mask.

2. The defect inspection method according to claim 1, wherein said patterns include multiple types of patterns which are formed on the wafer, and the reference image is generated using a plurality of images of regions having a same type of pattern.

3. The defect inspection method according to claim 2, wherein the wafer is a laminated semiconductor wafer formed by laminating a plurality of wafers having the multiple types of patterns formed thereon.

4. The defect inspection method according to claim 2, wherein the generating the reference image using the plurality of images of regions having the same type of pattern from among the multiple types of patterns formed thereon is performed in response to an input from a user or based on design data.

5. The defect inspection method according to claim 2, wherein the detecting the defect is performed by
   integrating features of a plurality of images of the regions having the same type of pattern from among the multiple types of patterns formed thereon with respect to each pixel in the plurality of images to calculate a reference value for each pixel;
   comparing the plurality of images with the calculated reference value,
   extracting a pixel exhibiting a largest deviation from the reference value as a candidate defect; and
   separating the extracted candidate defect into defective and non-defective using the multi-value mask.

6. The defect inspection method according to claim 3, wherein the wafer is a laminated semiconductor wafer formed by laminating a plurality of wafers having multiple types of patterns formed thereon, and
   wherein an internal defect is detected in an internal sectional image of the laminated semiconductor wafer parallel to the surface by
   applying the same labels to regions having the same combination of the patterns formed on the laminated plurality of wafers;
   generating a partial sectional image group comprising the regions applied with the same labels; and
   integrating the features of the partial sectional image in the partial sectional image group belonging to the respective labels.

7. A defect inspection apparatus comprising:
   a tank which is constructed to accept a wafer disposed on a bottom of the tank, wherein the bottom of the tank is filled with a medium, and the medium is capable of propagating an ultrasonic wave;
   a ultrasonic probe; and
   an image processor configured to
   obtain an image of the wafer having patterns formed thereon by
   (1) sending the ultrasonic wave to the wafer while scanning a plane parallel to a surface of the wafer with the ultrasonic probe;
   (2) receiving a reflected echo wave returned from the wafer to which the ultrasonic wave was sent using the ultrasonic probe; and
   (3) generating an image of the plane parallel to the surface in the wafer from the received reflected echo wave;
   generate a reference image that does not include a defect from the obtained image of the wafer;
   generate a multi-value mask for masking a non-defective pixel from the obtained image of the wafer;
   calculate a defect accuracy by matching a brightness of the image of the wafer and of the reference image; and
   detect a defect by comparing a calculated defect accuracy with the generated multi-value mask.

8. The defect inspection method according to claim 7, wherein said patterns include multiple types of patterns which are formed on the wafer, and the reference image is generated using a plurality of images of regions having a same type of pattern.

9. The defect inspection apparatus according to claim 8, wherein the wafer is a laminated semiconductor wafer formed by laminating a plurality of wafers having the multiple types of patterns formed thereon.

10. The defect inspection apparatus according to claim 8, wherein the generating the reference image using the plurality of images of regions having the same type of pattern from among the multiple types of patterns formed thereon is performed in response to an input from a user or based on design data.

11. The defect inspection apparatus according to claim 8, wherein the image processor is further configured to detect the defect by
    integrating features of a plurality of images of the regions having the same type of pattern from among the multiple types of patterns formed thereon with respect to each pixel in the plurality of images to calculate a reference value for each pixel;
    comparing the plurality of images with the calculated reference value;
    extracting a pixel exhibiting a largest deviation from the reference value as a candidate defect; and
    separating the extracted candidate defect into defective and non-defective using the multi-value mask.

12. The defect inspection apparatus according to claim 9, wherein the wafer is a laminated semiconductor wafer formed by laminating a plurality of wafers having multiple types of patterns formed thereon, and
    wherein an internal defect is detected in an internal sectional image of the laminated semiconductor wafer parallel to the surface by applying the same labels to regions having the same combination of the patterns formed on the laminated plurality of wafers;

generating a partial sectional image group comprising the regions applied with the same labels; and integrating the features of the partial sectional image in the partial sectional image group belonging to the respective labels.

13. A defect inspection apparatus comprising:

a tank which is constructed to accept a wafer disposed on a bottom of the tank, wherein the bottom of the tank is filled with a medium, and the medium is capable of propagating an ultrasonic wave;

a ultrasonic probe; and an image processor configured to obtain a sectional image of the wafer having patterns formed thereon by
(1) sending the ultrasonic wave to the wafer while scanning a plane which is inside the wafer and parallel to a surface of the wafer with the ultrasonic probe;
(2) receiving a reflected echo wave returned from the wafer to which the ultrasonic wave was sent using the ultrasonic probe; and
(3) generating a sectional image of the plane from the received reflected echo wave;

generate a reference image that does not include a defect from the obtained image of the wafer;

generate a multi-value mask for masking a non-defective pixel from the obtained image of the wafer;

calculate a defect accuracy by matching a brightness of the image of the wafer and of the reference image; and detect a defect by comparing a calculated defect accuracy with the generated multi-value mask.

14. The defect inspection apparatus according to claim 13, wherein the image processor is further configured to group the obtained sectional images into a plurality of partial sectional image groups each including regions generated by a same type of pattern;

generate the reference image is generated from each obtained partial sectional image; and generate the multi-value mask from the obtained internal sectional image, in each said partial sectional image group.

* * * * *